US010383938B2

(12) United States Patent
Wightman

(10) Patent No.: US 10,383,938 B2
(45) Date of Patent: Aug. 20, 2019

(54) LIPIDATED IMMUNE RESPONSE MODIFIER COMPOUND COMPOSITIONS, FORMULATIONS, AND METHODS

(71) Applicant: 3M Innovative Properties Company, St. Paul, MN (US)

(72) Inventor: Paul D. Wightman, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/043,394

(22) Filed: Jul. 24, 2018

(65) Prior Publication Data
US 2018/0326051 A1    Nov. 15, 2018

Related U.S. Application Data

(60) Continuation of application No. 15/822,556, filed on Nov. 27, 2017, now Pat. No. 10,052,380, which is a continuation of application No. 15/241,166, filed on Aug. 19, 2016, now abandoned, which is a continuation of application No. 14/969,483, filed on Dec. 15, 2015, now Pat. No. 9,795,669, which is a division of application No. 13/817,214, filed as application No. PCT/US2011/047901 on Aug. 16, 2011, now Pat. No. 9,242,980.

(60) Provisional application No. 61/374,512, filed on Aug. 17, 2010.

(51) Int. Cl.
| A61K 9/127 | (2006.01) |
| A61K 39/39 | (2006.01) |
| A61K 9/00 | (2006.01) |
| A61K 9/10 | (2006.01) |
| A61K 31/47 | (2006.01) |
| A61K 39/00 | (2006.01) |
| A61K 47/26 | (2006.01) |
| C07D 471/04 | (2006.01) |
| A61K 31/437 | (2006.01) |
| A61K 39/145 | (2006.01) |
| C12N 7/00 | (2006.01) |

(52) U.S. Cl.
CPC .......... *A61K 39/39* (2013.01); *A61K 9/0019* (2013.01); *A61K 9/10* (2013.01); *A61K 9/127* (2013.01); *A61K 31/437* (2013.01); *A61K 31/47* (2013.01); *A61K 39/0011* (2013.01); *A61K 39/145* (2013.01); *A61K 47/26* (2013.01); *C07D 471/04* (2013.01); *C12N 7/00* (2013.01); *A61K 2039/54* (2013.01); *A61K 2039/55511* (2013.01); *A61K 2039/55555* (2013.01); *A61K 2039/55572* (2013.01); *A61K 2039/572* (2013.01); *C12N 2760/16134* (2013.01); *Y02A 50/41* (2018.01); *Y02A 50/412* (2018.01)

(58) Field of Classification Search
None
See application file for complete search history.

(56) References Cited

U.S. PATENT DOCUMENTS

| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |

(Continued)

FOREIGN PATENT DOCUMENTS

| EP | 0 394 026 | 10/1990 |
| EP | 1 104 764 | 6/2001 |

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.
International Search Report for PCT/US2011/047901; dated Nov. 4, 2011.
Written Opinion for PCT/US2011/047901; dated Nov. 4, 2011.
Brennan et al., "Automated Bioassay of Interferons in Micro-test Plates.", *Biotechniques*, Jun./Jul., 78, 1983.
Testerman et al., "Cytokine Induction by the Immunomodulators Imiquimod and S-27609." *Journal of Leukocyte Biology*, vol. 58, pp. 365-372, Sep. 1995.
Bachman et al., "Synthesis of Substituted Quinolylamines. Derivatives of 4-Amino-7-Chloroquinoline.", *J. Org. Chem.* 15, pp. 1278-1284 (1950).

(Continued)

*Primary Examiner* — Nannette Holloman
(74) *Attorney, Agent, or Firm* — AstraZeneca Global IP

(57) ABSTRACT

The compound N-(4-{[4-amino-2-butyl-1H-imidazo[4,5-c] quinolin-1-yl]oxy}butyl)octadecanamide is a useful drug compound for enhancing immune response and can be used, for example, as a vaccine adjuvant and a cancer treatment.

12 Claims, No Drawings

(56) References Cited

U.S. PATENT DOCUMENTS

| | | |
|---|---|---|
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,906,506 B2 | 3/2011 | Griesgraber et al. |
| 7,915,281 B2 | 3/2011 | Moser et al. |
| 7,939,526 B2 | 5/2011 | Radmer et al. |
| 7,943,609 B2 | 5/2011 | Griesgraber et al. |
| 7,968,562 B2 | 6/2011 | Skwierczynski et al. |
| 7,968,563 B2 | 6/2011 | Kshirsager et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 8,034,938 B2 | 10/2011 | Griesgraber et al. |
| 9,242,980 B2 | 1/2016 | Wightman |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |

(56) References Cited

U.S. PATENT DOCUMENTS

| | | |
|---|---|---|
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0166384 A1 | 7/2007 | Zarraga et al. |
| 2007/0167479 A1 | 7/2007 | Busch et al. |
| 2007/0213355 A1 | 9/2007 | Capraro et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0005376 A1 | 1/2009 | Krepski et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |
| 2016/0175433 A1 | 6/2016 | Wightman |

FOREIGN PATENT DOCUMENTS

| | | |
|---|---|---|
| JP | 9-176116 | 7/1997 |
| JP | 9-208584 | 8/1997 |
| JP | 11-080156 | 3/1999 |
| JP | 11-222432 | 8/1999 |
| JP | 2000-247884 | 9/2000 |
| WO | WO 2002/036592 | 5/2002 |
| WO | WO 2004/032829 | 4/2004 |
| WO | WO 2005/003064 | 1/2005 |
| WO | WO 2005/018555 | 3/2005 |
| WO | WO 2005/051317 | 6/2005 |
| WO | WO 2006/028451 | 3/2006 |
| WO | WO 2006/028962 | 3/2006 |
| WO | WO 2006/063072 | 6/2006 |
| WO | WO 2006/121528 | 11/2006 |
| WO | WO 2007/030775 | 3/2007 |
| WO | WO 2012/167081 | 12/2012 |

OTHER PUBLICATIONS

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1 H-Imidazo[4,5-c]quinoline Derivatives as Novel Potent TNF-αSuppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

Gerster et al. "Synthesis and Structure" *J. Med Chem.* 2005, 48, 3481-3491.

Smirnov et al., "Vaccine Adjuvant Activity of 3M-052: An Imidazoquinoline Designed for Local Activity without Systemic Cytokine Induction", Vaccine 29, pp. 5434-5442 (2011).

LIPIDATED IMMUNE RESPONSE MODIFIER COMPOUND COMPOSITIONS, FORMULATIONS, AND METHODS

This application is a continuation of U.S. application Ser. No. 15/822,556 filed on Nov. 27, 2017, said application Ser. No. 15/822,556 is a continuation of U.S. application Ser. No. 15/241,166, filed Aug. 19, 2016, now abandoned, said application Ser. No. 15/241,166 is a continuation of U.S. application Ser. No. 14/969,483, filed Dec. 15, 2015, now U.S. Pat. No. 9,795,669 issued Oct. 24, 2017, said application Ser. No. 14/969,483 is a division of U.S. application Ser. No. 13/817,214, filed May 21, 2013, now U.S. Pat. No. 9,242,980 issued Jan. 26, 2016, said application Ser. No. 13/817,214 is a U.S. National Stage Application of International Application No. PCT/US2011/047901, filed Aug. 16, 2011, said International Application No. PCT/US2011/047901 claims benefit under 35 U.S.C. § 119(e) of the following U.S. Provisional Application Nos. 61/374,512 filed Aug. 17, 2010. Each of the above listed applications is incorporated by reference herein in its entirety for all purposes.

BACKGROUND

There has been an effort in recent years, with significant success, to discover new drug compounds that act by stimulating certain key aspects of the immune system, as well as by suppressing certain other aspects (see, e.g., U.S. Pat. No. 6,039,969 (Tomai et al.) and U.S. Pat. No. 6,200,592 (Tomai et al.). These compounds, referred to herein as immune response modifiers (IRMs), appear to act through basic immune system mechanisms known as Toll-like receptors (TLRs) to induce selected cytokine biosynthesis, induction of co-stimulatory molecules, and increased antigen-presenting capacity.

Many IRMs may be useful for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), $T_H2$-mediated diseases (e.g., asthma, allergic rhinitis, atopic dermatitis), and auto-immune diseases. Certain IRMs may also be useful, for example, as vaccine adjuvants.

Many known IRMs are imidazoquinoline amine derivatives (see, e.g., U.S. Pat. No. 4,689,338 (Gerster)), but other compound classes are known as well (see, e.g., U.S. Pat. No. 5,446,153 (Lindstrom et al.); U.S. Pat. No. 6,194,425 (Gerster et al.); and U.S. Pat. No. 6,110,929 (Gerster et al.); and International Publication Number WO2005/079195 (Hays et al.).

In view of the great therapeutic potential for IRMs in the treatment of a wide variety of diseases and conditions, and despite the important work that has already been done, new compounds that can effectively modulate the immune response, by induction of cytokine biosynthesis or other mechanisms, are still needed.

SUMMARY

The present invention provides, in one aspect, a new compound useful for inducing cytokine biosynthesis. The compound (i.e., N-(4-{[4-amino-2-butyl-1H-imidazo[4,5-c]quinolin-1-yl]oxy}butyl)octadecanamide has the following formula (I):

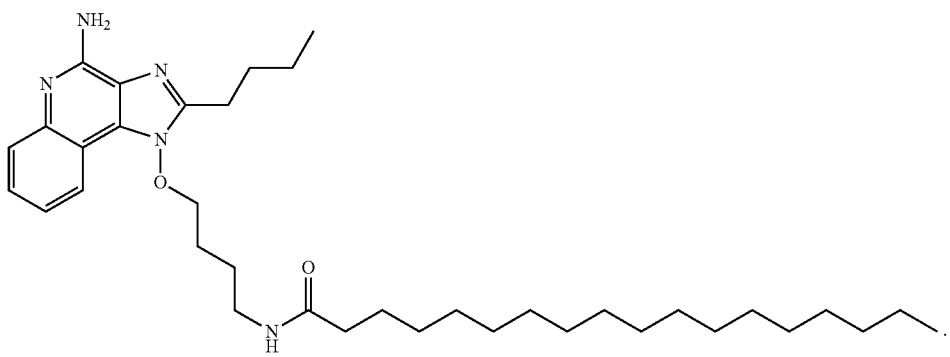 [SMILES: CCCCCCCCCCCCCCCCCC(=O)NCCCCOn1c(CCCC)nc2c(N)nc3ccccc3c21]

Pharmaceutically acceptable salts of the compound may also be used.

The compound of Formula I has unexpectedly beneficial properties in terms of biologic activity. It is particularly desirable for incorporation into liposome based formulations. It appears that such formulations are surprisingly effective at boosting localized immune response with reduced systemic TNF induction.

The ability to induce cytokine biosynthesis in animals makes the compound of Formula I useful for treating a variety of conditions such as viral diseases and tumors that are responsive to such changes in the immune response. Accordingly, the present invention further provides methods of inducing cytokine biosynthesis in an animal, treating a viral infection and/or treating a neoplastic disease in an animal by administering an effective amount of a compound of Formula I to the animal. The present invention further provides a method of vaccinating an animal comprising administering an effective amount of a compound of Formula I to the animal as a vaccine adjuvant.

The invention further provides pharmaceutical compositions comprising a pharmaceutically acceptable carrier and a therapeutically effective amount of a compound of Formula I. In some embodiments, the pharmaceutical composition further comprises an antigen (e.g., a vaccine). In some embodiments of the pharmaceutical composition, the compound of Formula I is incorporated in a homogeneously dispersed formulation. In some embodiments of the pharmaceutical composition, the compound of Formula I is incorporated in an emulsified formulation. In some embodiments of the pharmaceutical composition, the compound of Formula I is incorporated in an oil-in-water formulation (for example formulations comprising soybean oil, TWEEN 80, SPAN 85, and PBS). In some embodiments of the pharmaceutical composition, the compound of Formula I is incorporated into a liposome-based formulation.

Used as a vaccine adjuvant to an antigen vaccine, the compound of Formula I increases the antibody response to the vaccine. It can decrease the amount of antigen vaccine required to achieve a desired\therapeutically effective antibody response. For example, it can reduce the amount of vaccine antigen needed by 2-fold, 10-fold, 15-fold, 25-fold, 50-fold, or as much as 100-fold or more.

As illustrated in part by the non-limiting examples set forth herein, the compound of Formula I is useful for a wide range purposes, including but not limited to such things as a vaccine adjuvant for influenza vaccines. For example, when used as a vaccine adjuvant, the compound of Formula I in combination with an influenza vaccine antigen provides protection for H1N1 influenza infection (as well as influenza A, B, and swine flu). In particular, when used as a vaccine adjuvant, the compound of Formula I in combination with hemagglutinin antigens provides protection for H1N1 influenza infection.

The compound of Formula I induces cytokine production primarily at the site of administration (or at a local site of application) and can do so without substantial systemic cytokine induction, which may be important for reducing side effects. For example, the compound of Formula I can induce TNF production primarily at the site of administration (or at a local site of application) without inducing systemic TNF levels above the background level (i.e. the level measured systemically prior to administration of the compound of Formula I). In some applications subcutaneous injection of the compound of Formula I can be used to induce cytokine production (such as TNF production) in the local draining lymph nodes, but not peripheral lymph nodes. For example, subcutaneous injection of the compound of Formula I can induce cytokine production (such as TNF production) in the local draining lymph nodes at levels at least 2 times, 3 times, 5 times, 10 times, or as much as 100 times greater or more than in the peripheral lymph nodes In addition to the compound of Formula I, it is believed that the compound N-(4-{[4-amino-2-butyl-1H-imidazo[4,5-c]quinolin-1-yl]oxy}butyl)hexadecanamide may be synthesized using a similar synthetic route and may also be used for the same uses, pharmaceutical compositions, and formulations as the compound of Formula one set forth herein.

The terms "comprises" and variations thereof do not have a limiting meaning where these terms appear in the description and claims.

As used herein, "a", "an", "the", "at least one", and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

"Ameliorate" refers to any reduction in the extent, severity, frequency, and/or likelihood of a symptom or clinical sign characteristic of a particular condition.

"Antigen" refers to any substance that may be bound by an antibody in a manner that is immunospecific to some degree.

"Induce" and variations thereof refer to any measurable increase in cellular activity. For example, induction of an immune response may include, for example, an increase in the production of a cytokine, activation, proliferation, or maturation of a population of immune cells, and/or other indicator of increased immune function.

"Liposome" or "liposome based" as used herein refers generally to a self-assembling particle composed of amphipathic molecules such as, but not limited to lipid, lipid-like, or polymeric substances. They can also include lipopeptides and glycolipids.

"Symptom" refers to any subjective evidence of disease or of a patient's condition.

"Therapeutic" and variations thereof refer to a treatment that ameliorates one or more existing symptoms or clinical signs associated with a condition.

"Treat" or variations thereof refer to reducing, limiting progression, ameliorating, preventing, or resolving, to any extent, the symptoms or signs related to a condition.

The compound N-(4-{[4-amino-2-butyl-1H-imidazo[4,5-c]quinolin-1-yl]oxy}butyl)octadecanamide described herein may be in any of its pharmaceutically acceptable forms including solid, semi-solid, solvate (e.g., hydrate), wholly or partially dissolved (e.g., in a pharmaceutical composition), or dispersed in a pharmaceutically acceptable carrier. It will also be understood that any pharmaceutically acceptable salt form of the compound of Formula I N-(4-{[4-amino-2-butyl-1H-imidazo[4,5-c]quinolin-1-yl]oxy}butyl)octadecanamide may also be used.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION

Example 1

N-(4-{[4-amino-2-butyl-1H-imidazo[4,5-c]quinolin-1-yl]oxy}butyl)octadecanamide

Part A

A solution of valeric anhydride (6.03 g) and pyridine hydrochloride 0.198 in pyridine (8.28 g) was added to a solution of 3-amino-4-chloroquinoline (2.94 g) in pyridine (5.0 g) and the reaction was stirred at room temperature for 16 hours followed by heating at 60° C. for 3 hours. The reaction was concentrated under reduced pressure and sodium carbonate (15 mL of a 10% aqueous solution) was added. The reaction was stirred for 30 minutes and then filtered. The resulting solid was washed with water (60 mL) and dried under vacuum for 4 hours to provide 4.59 g of crude N-(4-chloroquinolin-3-yl)valeramide as brown flakes. The crude product was recrystallized from heptane (10 mL) and the recovered product was further purified by soxhlet extraction using refluxing heptane for 16 hours. The collection flask from the soxhlet extraction apparatus was cooled in a freezer for 2 hours. The resulting solid was collected by filtration and dried under vacuum to yield 2.00 g of N-(4-chloroquinolin-3-yl)valeramide as a white solid.

Part B

A solution of 4-amino-1-butanol (7.68 g) and pyridine (7.00 g) in dichloromethane (100 mL) was chilled in an ice bath and a solution of benzylchloroformate (14.37 g) in dichloromethane (100 mL) was slowly added with stirring over a period of thirty minutes. The ice bath was removed and the reaction was stirred for an additional 16 hours. Hydrochloric acid (1.2 M, 200 mL) was added and phases were separated. The organic phase was dried (MgSO$_4$), filtered and concentrated under reduced pressure. The resulting residue was recrystallized from toluene and dried under vacuum to provide 5.15 g of benzyl (4-hydroxybutyl)carbamate.

A solution of N-hydroxyphthalimide (3.36 g), benzyl (4-hydroxybutyl)carbamate (4.18 g) and triphenylphosphine (7.41 g) in dichloromethane (100 mL) was chilled in an ice bath and approximately two-thirds of a solution of diisopropylazodicarboxylate (DIAD, 5.68 g) in dichloromethane (50 mL) was slowly added with stirring. The internal temperature of the reaction was monitored and the addition of the DIAD solution was stopped when an exotherm could no longer be detected. The ice bath was removed and the reaction was allowed to warm to room temperature. The reaction was concentrated under reduced pressure and the resulting residue was dissolved in ethanol (200 proof, 100 mL). Hydrazine (1.98 g, 35% in water) was added and the reaction was stirred for 6 hours. The reaction was cooled in the freezer and the resulting solid was removed by filtration. The solid was washed with ethanol (50 mL). The combined filtrate was concentrated under reduced pressure and diethyl ether (100 mL) was added. Insoluble impurities were removed by filtration and 2.0 M HCl in ether (10 mL) was added to the solution. A precipitate formed immediately. The crude product was added to toluene (100 mL) and heated at reflux temperature for one hour. After cooling to room temperature, the solid product was recovered by filtration, washed with toluene, and dried under vacuum to yield 3.76 g of benzyl (4-aminooxybutyl)carbamate.

Part C

N-(4-chloroquinolin-3-yl)valeramide (1.97 g), benzyl (4-aminooxybutyl)carbamate (299 g), triethylamine (0.89 g) and 2-propanol (40.69 g) were combined and heated at 80° C. for 3.5 hours. The reaction was cooled to room temperature, filtered, and the filtrate concentrated under reduced pressure. Dichloromethane (20 mL) was added to the resulting solid and the mixture was stirred for twenty minutes. Undissolved solid was removed by filtration and the filtrate was washed with two 10 mL portions of water that had been made slightly acidic by the addition of 20 drops of hydrochloric acid (1.2 M). The organic fraction was dried and concentrated under reduced pressure. The crude solid was recrystallized from tetrahydrofuran to provide 2.56 g of benzyl 4-{[2-butyl-1H-imidazo[4,5-c]quinolin-1-yl]oxy}butylcarbamate.

Part D

Benzyl 4-{[2-butyl-1H-imidazo[4,5-c]quinolin-1-yl]oxy}butylcarbamate hydrochloride (10.05 g) was dissolved in dichloromethane (80 mL) and extracted with a solution of sodium carbonate (2.02 g) in 30 ml H$_2$O. The organic layer was cooled in an ice bath and a solution of m-chloroperbenzoic acid (5.93 g, 1.24 eq) dissolved in dichloromethane (30 mL) was slowly added. After 6 hr, ammonium hydroxide (10 mL of a 28-30% aqueous solution) was added to the reaction. A solution of benzenesulfonyl chloride (6.96 g) dissolved in 10 ml dichloromethane was slowly added with vigorous stirring. The cooling bath was removed and the reaction was stirred for an additional 12 hours. The reaction was diluted with water (100 mL) and the organic and aqueous fractions were separated. The aqueous fraction was extracted with dichloromethane (30 mL). The combined organic fractions were washed with two 90 ml portions of 5% sodium carbonate.

The dichloromethane solution was transferred to a distillation apparatus and 1-pentanol (50 mL) was added. This was warmed to 40° C. and the dichloromethane was removed under reduced pressure. Concentrated hydrochloric acid (50 ml) was then added and the reaction was stirred and heated to 80°. After 11 hours, the solution was cooled to room temperature and diluted with water (100 mL). The aqueous fraction was separated from the 1-pentanol and the 1-pentanol was extracted with water (25 mL). The aqueous fractions were combined. 1-Pentanol (50 mL) was added to the combined aqueous fraction and this was cooled in an ice-bath. With vigorous stirring, solid sodium carbonate was added to bring the pH to 9-10. The mixture was transferred to a separatory funnel and the fractions were separated. The aqueous fraction was extracted with two 25 ml portions of 1-pentanol. The combined 1-pentanol fractions were dried over sodium sulfate and filtered to provide 1-(4-aminobutoxy)-2-butyl-1H-imidazo[4,5-c]quinolin-4-amine dissolved in 1-pentanol.

The maleate salt of 1-(4-aminobutoxy)-2-butyl-1H-imidazo[4,5-c]quinolin-4-amine was prepared by dissolving maleic acid (4.83 g) in 1-pentanol (50 mL) and adding it with stirring to the solution of 1-(4-aminobutoxy)-2-butyl-1H-imidazo[4,5-c]quinolin-4-amine in 1-pentanol. The resulting precipitate was collected by filtration and dried to yield 7.69 g of 1-(4-aminobutoxy)-2-butyl-1H-imidazo[4,5-c]quinolin-4-amine bis maleate salt. $^1$H-NMR (DMSO-d6): δ 0.96 (t, 3H), 1.44 (m, 2H), 1.7-1.95 (m, 4H), 2.02 (m, 2H), 2.8-3.1 (m, 4H), δ 4.43 (t, 2H), 6.07 (s, 4H), 7.57 (t, 1H), 7.73 (t, 1H), 7.80 (d, 1H), 8.16 (d, 1H). Broad peaks for the ammonium protons are seen at approximately δ 7.8 and δ 8.7.

As an alternative the fumarate salt of 1-(4-aminobutoxy)-2-butyl-1H-imidazo[4,5-c]quinolin-4-amine was prepared by the following procedure. 1-(4-aminobutoxy)-2-butyl-1H-imidazo[4,5-c]quinolin-4-amine (6.53 g) was dissolved in 2-propanol (75 mL) and decolorizing carbon was added. The reaction was heated to reflux, filtered while hot, and cooled to room temperature. A solution of fumaric acid (2.5 g) in 2-propanol was added and the reaction was heated at reflux temperature for 5 minutes. Upon cooling to room temperature a precipitate formed. Filtration followed by drying the product under vacuum yielded 6.6 g of 1-(4-aminobutoxy)-

2-butyl-1H-imidazo[4,5-c]quinolin-4-amine fumarate. $^1$H-NMR (DMSO-d6): δ 0.95 (t, 3H), 1.42 (m, 2H), 1.70-1.92 (m, 4H), 1.92-2.10 (m, 2H), 2.85-3.05 (m, 4H), 4.34 (t, 3H), δ 6.46 (s, 2H), 7.30 (t, 1H), 7.47 (t, 1H), 7.60 (d, 1H), 8.02 (d, 1H). A broad ammonium peak appears at δ 6.77.

Part E 1-(4-Aminobutoxy)-2-butyl-1H-imidazo[4,5-c]quinolin-4-amine fumarate (1.30 g) was dissolved in dichloromethane (25 mL) and the solution washed with 3×15 ml portions of saturated sodium carbonate. The organic fraction was then washed with 15 ml saturated sodium chloride and dried over MgSO$_4$. The solution was filtered, the solvent removed under reduced pressure and the product was dried under vacuum to give 0.79 g of 1-(4-aminobutoxy)-2-butyl-1H-imidazo[4,5-c]quinolin-4-amine as the free base.

The 1-(4-aminobutoxy)-2-butyl-1H-imidazo[4,5-c]quinolin-4-amine was dissolved in dichloromethane (20 mL) and methanol (5 mL). Stearic acid (0.71 g) was added and the reaction was stirred to dissolve the stearic acid. 1-Ethyl-3-(3-dimethylaminopropyl) carbodiimide HCl (EDC, 0.45 g) was added and the reaction was stirred at ambient temperature for 16 hours. An additional portion of EDC was added (0.23 g) and the reaction was stirred for an additional 24 hours. Final portions of stearic acid (0.22 g) and EDC (0.37 g) were added to drive the reaction to completion and the reaction was stirred at ambient temperature for another 24 hours. The reaction was concentrated under reduced pressure and the resulting residue was purified by flash column chromatography using a Biotage chromatography system (Si40+ M2358-1 SiGel column, 85:15 dichloromethane/methanol isocratic elution). The semi-pure product was purified by flash column chromatography two more times using a 90:10 dichloromethane/methanol isocratic elution, followed by a 95:5 dichloromethane/methanol isocratic elution. The fractions containing product were concentrated to yield 1.12 g of N-(4-{[4-amino-2-butyl-1H-imidazo[4,5-c]quinolin-1-yl]oxy}butyl)octadecanamide as an off white waxy solid.

$^1$H-NMR (CDCl$_3$): δ 0.89 (t, 3H), 1.01 (t, 3H), 1.14-1.42 (m, 28H), 1.50 (m, 2H), 1.65 (m, 2H), 1.74-1.94 (m, 4H), 2.02 (m, 2H), 2.20 (t, 2H), 2.95 (t, 2H), 3.40 (q, 2H), 4.33 (t, 2H), 5.59 (t, 1H), 6.10 (broad s, 2H), 7.39 (m, 1H), δ 7.57 (m, 1H), 7.83 (d, 1H), 8.07 (m, 1H).

Example 2

The vaccine adjuvant activity of N-(4-{[4-amino-2-butyl-1H-imidazo[4,5-c]quinolin-1-yl]oxy}butyl)octadecanamide (Cmpd of Example 1) was evaluated in mice immunized with recombinant hemagglutinin 1 (HA). IgG2a antigen specific antibody response was measured using five different preparations (1. HA alone (control); 2. HA+resiquimod (comparator preparation); 3. HA+Cmpd of Example 1 formulated in dioleoylphosphatidylcholine (DOPC) (liposome formulation); 3. HA+Cmpd of Example 1; 5. HA+DOPC (control).

The Cmpd of Example 1 and resiquimod were individually prepared as aqueous suspensions in phosphate buffered saline (PBS). The Cmpd of Example 1 formulated in DOPC liposome formulation was prepared as follows. A stock solution of the Cmpd of Example 1 was prepared in chloroform at a concentration of 10 mg/ml. A stock solution of dioleoylphosphatidylcholine (DOPC) was also prepared in chloroform at a concentration of 10 mg/ml. Aliquots of each stock solution were combined to provide a solution containing DOPC and the Cmpd of Example 1 at a mass ratio of 10:1, respectively. The solution was blown to dryness and resuspended in sterile PBS by probe sonication.

Groups of 5 mice each were immunized subcutaneously with 10 μg of HA antigen in PBS, alone or in combination with 1 mg/Kg of the compounds cited in Table 1. DOPC control animals received the same amount of DOPC as that prepared with the Cmpd of Example 1. The mice were boosted with the same combinations 2 weeks and 4 weeks following the initial immunization. At 7 weeks post immunization, the mice were bled and the HA-specific IgG2a titers were determined. This determination was performed by serial dilution of the serum samples by standard serum ELISA in HA-coated microtiter plates. IgG2a data is presented as the serum dilution achieving the end point (2× baseline) and is the geometric mean for the 5 mice per group.

TABLE 1

| In Vivo Immunization Group | HA Specific IgG2a, Serum Dilution End Point |
|---|---|
| HA | 3.30E+03 |
| HA + Resiquimod | 1.00E+05 |
| HA + Cmpd of Example 1/DOPC | 3.30E+06 |
| HA + Cmpd of Example 1 | 1.42E+04 |
| HA + DOPC | 5.00E+03 |

Example 3

Antigen dependent interferon-gamma (IFNgamma) responses were determined in splenocyte cultures established from the same animals for which IgG2a antibody responses were determined in Example 2. The spleens from the animals were removed, combined to form two pools for each group of 5 animals, minced to create single cell suspensions, and placed in culture in 96 well microtiter plates. Each pool generated three wells for a control PBS challenge and three wells for a 10 mg HA challenge. The cultures were then incubated at 37° C. for 72 hours. The medium was then removed and the interferon-gamma generated was measured (pg/ml) by an ELISA assay (Table 2). The IFNgamma data is reported as the geometric mean value for each pool using triplicate measurements.

TABLE 2

| | In Vitro Challenge of Isolated Spleenocytes, (IFNgamma, pg/ml) | |
|---|---|---|
| In Vivo Immunization Group | Control PBS Challenge | HA Antigen Challenge |
| HA | 4.32 | 157.87 |
| HA + Resiquimod | 3.84 | 91.88 |
| HA + Cmpd of Example 1/DOPC | 5.84 | 1808.19 |
| HA + Cmpd of Example 1 | 4.82 | 293.51 |
| HA + DOPC | 1.7 | 231.97 |

Example 4

The effect of N-(4-{[4-amino-2-butyl-1H-imidazo[4,5-c]quinolin-1-yl]oxy}butyl)octadecanamide (Cmpd of Example 1) to induce the formation of systemic tumor necrosis factor (TNF) in vivo was evaluated in mice. Systemic TNF induction was measured using four different preparations (1. PBS (control); 2. resiquimod (comparator preparation); 3. resiquimod formulated in dioleoylphosphatidylcholine (DOPC) (comparator preparation); 4. Cmpd of Example 1 formulated in dioleoylphosphatidylcholine (DOPC) (liposomes).

Compound of Example 1 formulated in dioleoylphosphatidylcholine (DOPC) liposomes was prepared as described in Example 2. Resiquimod formulated in DOPC was prepared in an analogous manner to the Cmpd of Example 1 in DOPC. The resiquimod preparation was made as an aqueous suspension in PBS.

Mice were injected subcutaneously with preparations containing 1 mg/Kg of each test compound (i.e. resiquimod or Cmpd of Example 1). At one hour and at three hours post dose, the mice were bled and systemic TNF was measured in the serum (pg/mL) by ELISA assay. The results are presented as the geometric means obtained for each group of five animals. The data in Table 3 shows that subcutaneous injection of resiquimod in various formulations induces a systemic TNF response, while N-(4-{[4-amino-2-butyl-1H-imidazo[4,5-c]quinolin-1-yl]oxy}butyl)octadecanamide (Cmpd of Example 1) does not induce a systemic TNF response. This can be important in providing localized immune system enhancement without systemic TNF side effects.

TABLE 3

| Treatment | TNF concentration (pg/mL) at Times Following Treatment | |
|---|---|---|
| | 1 hour | 3 hour |
| PBS | <5 | <5 |
| Resiquimod | 1140.41 | <5 |
| Resiquimod/DOPC | 647.67 | <5 |
| Cmpd of Example 1/DOPC | <5 | <5 |

Example 5

Groups of 5 mice each were immunized subcutaneously with 10 μg of HA antigen, alone or with increasing amounts of N-(4-{[4-amino-2-butyl-1H-imidazo[4,5-c]quinolin-1-yl]oxy}butyl)octadecanamide (Cmpd of Example 1)/DOPC as cited in Table 4. The mice were boosted with the same combinations 2 weeks and 4 weeks following initial immunization. At 7 weeks post immunization, the mice were bled and the HA-specific IgG2a titers were determined. This determination was performed by serial dilution of the serum samples by standard serum ELISA in HA-coated microtiter plates. IgG2a data is the serum dilution achieving the end point (2× baseline) and is the geometric mean for the 5 mice per group.

TABLE 4

| In Vivo Immunization Group | HA Specific IgG2a, Serum Dilution End Point |
|---|---|
| Phosphate Buffered Saline (PBS) | <50 |
| HA | 5.0E+03 |
| HA + Cmpd of Example 1 (1.0 MPK)/DOPC | 2.5E+05 |
| HA + Cmpd of Example 1 (0.3 MPK)/DOPC | 1.3E+06 |
| HA + Cmpd of Example 1 (0.1 MPK)/DOPC | 1.1E+06 |
| HA + Cmpd of Example 1 (0.03 MPK)/DOPC | 5.0E+05 |
| HA + Cmpd of Example 1 (0.01 MPK)/DOPC | 2.5E+05 |

Example 6

Antigen dependent interferon-gamma (IFNgamma) responses were determined in splenocyte cultures established from the same animals for which IgG2a antibody responses were determined in Example 5. The spleens from the animals were removed, combined to form two pools for each group of 5 animals, minced to create single cell suspensions, and placed in culture in 96 well microtiter plates. Each pool generated three wells for a control PBS challenge and three wells for a 10 mg HA challenge. The cultures were then incubated at 37° C. for 72 hours. The medium was then removed and the interferon-gamma generated was measured (pg/ml) by an ELISA assay (Table 5). The IFNgamma data is reported as the geometric mean value for each pool using triplicate measurements.

TABLE 5

| | In Vitro Challenge of Isolated Spleenocytes, (IFNgamma, pg/ml) | |
|---|---|---|
| In Vivo Immunization Group | Control PBS Challenge | HA Antigen Challenge |
| Phosphate Buffered Saline (PBS) | 199.50 | 224.37 |
| HA | 189.74 | 236.64 |
| HA + Cmpd of Example 1 (1.0 MPK)/DOPC | 194.80 | 278.87 |
| HA + Cmpd of Example 1 (0.3 MPK)/DOPC | 184.23 | 861.42 |
| HA + Cmpd of Example 1 (0.1 MPK)/DOPC | 189.74 | 805.00 |
| HA + Cmpd of Example 1 (0.03 MPK)/DOPC | 179.44 | 1219.23 |
| HA + Cmpd of Example 1 (0.01 MPK)/DOPC | 204.82 | 1167.97 |

Example 7

The ability of N-(4-{[4-amino-2-butyl-1H-imidazo[4,5-c]quinolin-1-yl]oxy}butyl)octadecanamide (Cmpd of Example 1) to induce tumor necrosis factor (TNF) production in human peripheral mononuclear cells (PBMC) was determined. The human peripheral blood mononuclear cells were prepared from human volunteers and placed in culture in 96 well microtiter plates. The Cmpd of Example 1 was added to the wells at the following concentrations: 30, 10, 3.3, 1.1, 0.37, 0.13, 0.043, and 0.014 μM. The cells were then incubated overnight at 37° C. The medium was removed and TNF concentration (ng/mL) was measured by ELISA assay (Table 6).

TABLE 6

| Cmpd of Example 1 Concentration μM | TNF ng/mL |
|---|---|
| 0.014 | 0.13 |
| 0.043 | 0.17 |
| 0.13 | 0.35 |
| 0.37 | 2.51 |
| 1.1 | 7.07 |
| 3.3 | 28.73 |
| 10 | 31.46 |
| 30 | 29.47 |

Example 8

The viral protection activity of N-(4-{[4-amino-2-butyl-1H-imidazo[4,5-c]quinolin-1-yl]oxy}butyl)octadecanamide (Cmpd of Example 1) was evaluated in Balb/c male mice (Charles River, Wilmington, Mass.) infected intranasally with mouse-adapted H1N1 A/Puerto Rico/8/34 (obtained from American Type Culture Collection, Manassas, Va.). Four weeks prior to infection, groups of 10 mice each were immunized with 1. PBS; 2. 10 µg HA; or 3. 10 µg HA+0.1 mg/Kg of Cmpd of Example 1 in DOPC liposomes, respectively. Two weeks prior to infection, the same groups were boosted with their corresponding immunizing doses. Survival of mice was monitored for 11 days following intranasal infection and the data is presented in Table 7 as percent survival on each day. One mouse from group 1, and two mice from group 2 failed to achieve infection as determined from lack of weight loss within the first 3 days of infection. Therefore, by day 5 group 1 was comprised of 9 mice, group 2 was comprised of 8 mice, and groups 3 and 4 were comprised of 10 mice, each.

TABLE 7

| | Immunization Group (Percent Survival) | | |
|---|---|---|---|
| Day | PBS | HA | HA + Cmpd of Example 1 |
| 1 | 100 | 100 | 100 |
| 2 | 100 | 100 | 100 |
| 3 | 100 | 100 | 100 |
| 4 | 100 | 100 | 100 |
| 5 | 100 | 100 | 100 |
| 6 | 100 | 100 | 100 |
| 7 | 77.8 | 100 | 100 |
| 8 | 66.7 | 75.0 | 100 |
| 9 | 44.4 | 75.0 | 100 |
| 10 | 11.1 | 50.0 | 100 |
| 11 | 0 | 50.0 | 100 |

Example 9

The immune activation activity of N-(4-{[4-amino-2-butyl-1H-imidazo[4,5-c]quinolin-1-yl]oxy}butyl)octadecanamide (Cmpd of Example 1) was evaluated in a mouse prophylactic anti-tumor immunization model. Groups of C57/B1 male mice (Charles River, Wilmington, Mass.) were immunized and boosted twice at two week intervals with 1) PBS; 2) 20 µg ovalbumin; or 3) 20 µg ovalbumin+1.0 mg/Kg Cmpd of Example 1. One week following the final boost, each mouse was injected intradermally with 4E5 B16Ova melanoma tumor cells. Mice were sacrificed 11 days following tumor injection, tumors were measured at their major and minor diameters, and the products of the two measurements were determined. The mean tumor size in mm$^2$+/- standard deviation (s.d.) for each group was determined. The results are presented in Table 8.

TABLE 8

| Immunization Material | Number of Mice | Mean Tumor Size (s.d.) |
|---|---|---|
| PBS | 7 | 10.21 (4.34) |
| Ovalbumin | 8 | 10.18 (8.95) |
| Ovalbumin + Cmpd of Example 1 | 8 | 0.99 (0.81) |

Example 10

The dose sparing activity of N-(4-{[4-amino-2-butyl-1H-imidazo[4,5-c]quinolin-1-yl]oxy}butyl)octadecanamide (Cmpd of Example 1) was evaluated in mice immunized with varying amounts of HA with and without Cmpd of Example 1. Groups of five Balb/c male mice (Charles River, Wilmington, Mass.) were immunized with 1 µg, 5 µg, or 15 µg of HA with or without 0.1 mg/kg of Cmpd of Example 1. The mice were then boosted with the same preparations at 2 weeks and at 4 weeks post immunization. Three weeks following the final boost, the mice were bled and titers of HA-specific IgG1 and IgG2a were determined by serial dilution of the serum samples using a standard serum ELISA assay in HA-coated microtiter plates. The IgG1 and IgG2a data is presented in Table 9 as the serum dilution that achieved the end point (2x baseline) and is the geometric mean for 5 mice per group. The addition of 0.1 mg/Kg of Cmpd of Example 1 to HA greatly enhanced the antibody response to this antigen.

TABLE 9

| Immunization Group | IgG1 End Point | IgG2a End Point |
|---|---|---|
| HA 1 µg | 2.5E4 | 3.3E2 |
| HA 5 µg | 6.7E4 | 1.0E3 |
| HA 15 µg | 6.7E4 | 2.5E3 |
| HA 1 µg + Cmpd of Example 1 | 1.7E7 | 3.3E6 |
| HA 5 µg + Cmpd of Example 1 | 1.4E7 | 2.5E7 |
| HA 15 µg + Cmpd of Eaxmple 1 | 1.1E7 | 1.0E8 |

Example 11

The local in vivo activity of N-(4-{[4-amino-2-butyl-1H-imidazo[4,5-c]quinolin-1-yl]oxy}butyl)octadecanamide (Cmpd of Example 1) was evaluated in groups of four Balb/c male mice (Charles River) and compared to the activity of resiquimod (a comparator compound). Solutions of the Cmpd of Example 1 or resiquimod were injected subcutaneously into four separate groups of mice for evaluation at the time points of 1 hour, 3 hour, 6 hours, and 18 hours post dose. The final dose for either compound was 1.0 mg/kg. At each time point, the mice were bled, sacrificed, and the draining axial and brachial lymph nodes were removed and placed in RNA preservation fluid (RNA later reagent obtained from Ambion Corporation, Austin, Tex.). Serum samples were analyzed for TNF protein concentration (pg/ml) by ELISA as a measure of systemic presence of this cytokine. The draining lymph nodes were processed for measurement of TNF mRNA gene expression by quantitative PCR (7900HT Thermocycler obtained from Applied Biosystems, Carlsbad, Calif.). The data reported (Table 10) is the mean+/-standard deviation (s.d.) for each group. The "not detected" level for serum TNF concentration was less than 10 pg/ml. The induction of TNF mRNA gene expression in the draining lymph nodes without detection of TNF protein in the serum after the injection of the Cmpd of Example 1 demonstrates that the cytokine induction effects of the Cmpd of Example 1 are primarily local.

TABLE 10

| | Serum TNF [pg/ml (s.d.)] | | TNF mRNA Gene Expression in Lymph Nodes [fold increase versus naïve control (s.d.)] | |
|---|---|---|---|---|
| Time (hours) | Cmpd of Example 1 | Resiquimod | Cmpd of Example 1 | Resiquimod |
| 1 | not detected | 4082 (873) | 0.65 (0.04) | 14.19 (3.83) |
| 3 | not detected | 107 (35) | 1.62 (1.23) | 4.82 (0.70) |
| 6 | not detected | 18 (4) | 7.23 (2.07) | 1.39 (0.27) |
| 18 | not detected | not detected | 1.55 (0.28) | 0.90 (0.23) |

The present invention thus provides the compound of Formula I, as well as pharmaceutical compositions and formulations thereof. In some embodiments, the compound of Formula I is incorporated into a liposome based formulation. One may also incorporate an antigen admixed with or administered separately but in combination with such formulation. For example, an antigen may be formulated within the lumen of the self-assembling liposome particle. Such liposomes would include composites of such substances in proportions best suited to yield stable particles of desired sizes and diameters. Sizes can be of the sub micron range to mimic viral pathogens and micron size to mimic bacterial antigens. These sizes can be controlled by particle composition and process of formation.

In some embodiments of the methods disclosed herein, the compound of Formula I (e.g., in a pharmaceutical composition disclosed herein) is administered to a localized tissue region, such as into a tumor mass. In some of these embodiments, the compound of Formula I is administered to localized tissue, such as a tumor mass, in a liposome formulation. A cancer vaccine may also be included.

A "localized tissue region" will generally be a relatively small portion of the body, e.g., less than 10 percent by volume, and often less than 1 percent by volume. For example, depending on the size of, e.g., a solid tumor or cancerous organ, the localized tissue region will typically be on the order of no more than about 500 cubic centimeters ($cm^3$), often less than about 100 $cm^3$, and in many instances 10 $cm^3$ or less. For some applications the localized tissue region will be 1 $cm^3$ or less (e.g., for small tumor nodules, viral lesions, or vaccination sites). However, in certain instances the localized tissue region may be a particularly large region, up to several liters, for example, to treat metastasized cancer within the entire peritoneal cavity. The localized tissue region may be, for example, a cancer, a viral infected lesion, or organ, or vaccination site. It may be, for example, a solid tumor, lymph tissue, reticuloendothelial system, bone marrow, mucosal tissue, etc. The localized tissue region may be, e.g., a breast cancer tumor, stomach cancer tumor, lung cancer tumor, head or neck cancer tumor, colorectal cancer tumor, renal cell carcinoma tumor, pancreatic cancer tumor, basal cell carcinoma tumor, cervical cancer tumor, melanoma cancer tumor, prostate cancer tumor, ovarian cancer tumor, or bladder cancer tumor. Delivery of the compound of Formula I to a localized tissue region may be in conjunction with image guiding techniques using, for example, ultrasound, MRI, and real-time X-ray (fluoroscopy).

In some embodiments of the pharmaceutical compositions and methods disclosed herein, the pharmaceutical composition further comprises an antigen in an amount effective to generate an immune response against the antigen. In some embodiments, the antigen is a vaccine. Vaccines include any material administered to raise either humoral and/or cell mediated immune response, such as live or attenuated viral and bacterial immunogens and inactivated viral, tumor-derived, protozoal, organism-derived, fungal, and bacterial immunogens, toxoids, toxins, polysaccharides, proteins, glycoproteins, peptides, cellular vaccines (e.g., using dendritic cells), DNA vaccines, recombinant proteins, glycoproteins, and peptides. Exemplary vaccines include vaccines for cancer, BCG, cholera, plague, typhoid, hepatitis A, B, and C, influenza A and B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, severe acute respiratory syndrome (SARS), anthrax, and yellow fever. See also, e.g., vaccines disclosed in International Publication No. WO 02/24225 (Thomsen et al.).

Antigens can be co-delivered with a compound of Formula I, for example, in admixture in a pharmaceutical composition according to the present invention. Such pharmaceutical compositions may include the compound in Formula I in liposomes. This may allow the compound of Formula I to reach, for example, antigen presenting cells at or around the same time as the antigen. In other embodiments, the compound of Formula I and the antigen may be administered separately at or about the same time. Co-delivering a vaccine adjuvant (e.g., an IRM compound such as a compound of Formula I) and an antigen to an immune cell can increase the immune response to the antigen and improve antigen-specific immunological memory. Optimal delivery may occur, for example, when the adjuvant and the antigen are processed within an antigen presenting cell at the same time.

In addition to the delivery methods mentioned specifically above, a compound of Formula I (e.g., in a pharmaceutical composition disclosed herein) may be administered in any other suitable manner (e.g., non-parenterally or parenterally). As used herein, non-parenterally refers to administration through the digestive tract, including by oral ingestion. Parenterally refers to administration other than through the digestive tract which would include nasal (e.g., transmucosally by inhalation), topical, ophthalmic, and buccal administration, but in practice usually refers to injection (e.g., intravenous, intramuscular, subcutaneous, intratumoral, or transdermal) using, for example, conventional needle injection, injection using a microneedle array, or any other known method of injection.

The compound of Formula I may be provided in any pharmaceutical composition suitable for administration to a subject and may be present in the pharmaceutical composition in any suitable form (e.g., a solution, a suspension, an emulsion, or any form of mixture). The pharmaceutical composition may be formulated with any pharmaceutically acceptable excipient, carrier, or vehicle. In some embodiments, the pharmaceutically acceptable carrier comprises water (e.g., phosphate or citrate buffered saline). In some embodiments, the pharmaceutically acceptable carrier comprises an oil (e.g., corn, sesame, squalene, cottonseed, soybean, or safflower oil). The pharmaceutical composition may further include one or more additives including skin penetration enhancers, colorants, fragrances, flavorings, moisturizers, thickeners, suspending agents, surfactants, and dispersing agents.

In addition to antigens specifically described above, the pharmaceutical compositions and methods of the present disclosure can include other additional active agents, e.g., in admixture or administered separately. Such additional agents can include a chemotherapeutic agent, a cytotoxoid agent, an antibody, an antiviral agent, a cytokine, a tumor necrosis factor receptor (TNFR) agonist, or an additional immune response modifier. TNFR agonists that may be delivered in conjunction with the compound of Formula I include CD40 receptor agonists, such as disclosed in copending application U.S. Patent Publication 2004/0141950 (Noelle et al.). Other active ingredients for use in combination with an IRM preparation of the present invention include those disclosed in, e.g., U.S. Patent Publication No. 2003/0139364 (Krieg et al.).

In some embodiments, a pharmaceutical composition according to the present invention may be a conventional topical dosage formulation (e.g., a cream, an ointment, an aerosol for inflation, a non-aerosol spray, a gel, or a lotion). Suitable types of formulations are described, for example, in U.S. Pat. No. 5,238,944 (Wick et al.); U.S. Pat. No. 5,939,090 (Beaurline et al.); U.S. Pat. No. 6,245,776 (Skwierczynski et al.); European Patent No. EP 0394026 (Schultz); and U.S. Patent Publication No. 2003/0199538 (Skwierczynski et al.).

The compound of Formula I has been shown to induce the production of TNF-α as described above. The ability to induce TNF production indicates that the compound of Formula I is useful as an immune response modifier that can modulate the immune response in a number of different ways, rendering it useful in the treatment of a variety of disorders. Other cytokines whose production may be induced by the administration of the compound of Formula I generally include Type I interferons (e.g., INF-α), IL-1, IL-6, IL-8, IL-10, IL-12, MIP-1, MCP-1, and a variety of other cytokines. Among other effects, these and other cytokines inhibit virus production and tumor cell growth, making the compound of Formula I useful in the treatment of viral diseases and neoplastic diseases. Accordingly, the invention provides a method of inducing cytokine biosynthesis in an animal comprising administering an effective amount of the compound of Formula I (e.g., in a pharmaceutical composition) to the animal. The animal to which the compound of Formula I is administered for induction of cytokine biosynthesis may have a disease (e.g., a viral or neoplastic disease), and administration of the compound may provide therapeutic treatment. Also, the compound of Formula I may be administered to the animal before the animal acquires the disease so that administration of the compound of Formula I may provide a prophylactic treatment.

In addition to the ability to induce the production of cytokines, the compound of Formula I may affect other aspects of the innate immune response. For example, natural killer cell activity may be stimulated, an effect that may be due to cytokine induction. IRM activity of the compound of Formula I also may include activating macrophages, which in turn stimulate secretion of nitric oxide and the production of additional cytokines. IRM activity of the compound of Formula I also may include inducing cytokine production by T cells, activating T cells specific to an antigen, and/or activating dendritic cells. Further, IRM activity of the compound of Formula I may include proliferation and differentiation of B-lymphocytes. IRM activity of the compound of Formula I also may affect the acquired immune response. For example, IRM activity can include inducing the production of the T helper type 1 ($T_H1$) cytokine IFN-γ and/or inhibiting the production of the T helper type 2 ($T_H2$) cytokines IL-4, IL-5 and/or IL-13.

Exemplary conditions that may be treated by administering the compound of Formula I include:

(a) viral diseases such as diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as diseases resulting from infection by bacteria of, for example, the genus *Escherichia*, *Enterobacter*, *Salmonella*, *Staphylococcus*, *Shigella*, *Listeria*, *Aerobacter*, *Helicobacter*, *Klebsiella*, *Proteus*, *Pseudomonas*, *Streptococcus*, *Chlamydia*, *Mycoplasma*, *Pneumococcus*, *Neisseria*, *Clostridium*, *Bacillus*, *Corynebacterium*, *Mycobacterium*, *Campylobacter*, *Vibrio*, *Serratia*, *Providencia*, *Chromobacterium*, *Brucella*, *Yersinia*, *Haemophilus*, or *Bordetella*;

(c) other infectious diseases such as chlamydia, fungal diseases (e.g., candidiasis, aspergillosis, histoplasmosis, or cryptococcal meningitis), or parasitic diseases (e.g., malaria, pneumocystis carnii pneumonia, leishmaniasis, cryptosporidiosis, toxoplasmosis, and trypanosome infection);

(d) neoplastic diseases such as intraepithelial neoplasias, cervical dysplasia, actinic keratosis, basal cell carcinoma, squamous cell carcinoma, renal cell carcinoma, Kaposi's sarcoma, melanoma, leukemias (e.g., myelogenous leukemia, chronic lymphocytic leukemia, multiple myeloma, non-Hodgkin's lymphoma, cutaneous T-cell lymphoma, B-cell lymphoma, and hairy cell leukemia), breast cancer, lung cancer, prostate cancer, colon cancer, and other cancers;

(e) $T_H2$-mediated, atopic diseases such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, and alopecia areata; and (g) diseases associated with wound repair such as inhibition of keloid formation and other types of scarring (e.g., enhancing wound healing, including chronic wounds).

The mechanism for the antiviral and antitumor activity of the compound of Formula I may be due in substantial part to enhancement of the immune response by induction of various important cytokines (e.g., at least one of tumor necrosis factor, interferons, or interleukins). Such compounds have been shown to stimulate a rapid release of certain monocyte/macrophage-derived cytokines and are also capable of stimulating B cells to secrete antibodies which play an important role in these IRM compounds' antiviral and antitumor activities.

It will be understood that in the treatment of the diseases mentioned above, for example, the compound of Formula I can be used in combination with other therapies such as the active agents mentioned above and other procedures (e.g., chemoablation, laser ablation, cryotherapy, and surgical excision).

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-1O and IL-12 that is increased over a background level of such cytokines. The precise amount will vary according to factors known in the art but is expected to be a dose of about 100 nanograms per kilograms (ng/kg) to about 50 milligrams per kilogram (mg/kg), in some embodiments about 10 micrograms per kilogram (μg/kg) to about 5 mg/kg. The invention also provides a method of treating a viral infection in an animal and a method of treating a neoplastic disease in an animal comprising administering an effective amount of a compound or pharmaceutical composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, in some embodiments about 10 µg/kg to about 5 mg/kg. An amount of a compound or pharmaceutical composition effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, in some embodiments about 10 µg/kg to about 5 mg/kg. The methods of the present invention may be performed on any suitable subject. Suitable subjects include animals such as humans, non-human primates, rodents, dogs, cats, horses, pigs, sheep, goats, or cows.

The composition of a formulation suitable for practicing the invention, the precise amount of a compound of Formula I effective for methods according to the present invention, and the dosing regimen, for example, will vary according to factors known in the art including the nature of the carrier, the state of the subject's immune system (e.g., suppressed, compromised, stimulated), the method of administering the compound of Formula I, and the species to which the formulation is being administered. Accordingly, it is not practical to set forth generally the composition of a formulation that includes a compound of Formula I, an amount of a compound of Formula I that constitutes an effective amount, or a dosing regimen that is effective for all possible applications. Those of ordinary skill in the art, however, can readily determine appropriate formulations, amounts of the compound of Formula I, and dosing regimen with due consideration of such factors.

In some embodiments, the methods of the present invention include administering a compound of Formula I to a subject in a formulation, for example, having a concentration of the compound from about 0.0001% to about 20% (unless otherwise indicated, all percentages provided herein are weight/weight with respect to the total formulation), although in some embodiments the compound of Formula I may be administered using a formulation that provides the compound in a concentration outside of this range. In some embodiments, the method includes administering to a subject a formulation that includes from about 0.01% to about 1% of the compound of Formula I, for example, a formulation that includes about 0.1% to about 0.5% compound of Formula I.

In some embodiments, the methods of the present invention include administering sufficient compound to provide a dose of, for example, from about 100 ng/kg to about 50 mg/kg to the subject, although in some embodiments the methods may be performed by administering compound in a dose outside this range. In some of these embodiments, the method includes administering sufficient compound to provide a dose of from about 10 µg/kg to about 5 mg/kg to the subject, for example, a dose of from about 100 µg/kg to about 1 mg/kg. In some embodiments, the methods of the present invention may include administering sufficient compound to provide a dose of, for example, from about 0.01 mg/m² to about 10 mg/m². Alternatively, the close may be calculated using actual body weight obtained just prior to the beginning of a treatment course. For the dosages calculated in this way, body surface area (m²) is calculated prior to the beginning of the treatment course using the Dubois method: m²=(wt kg$^{0.425}$×height cm$^{0.725}$)×0.007184.

In some embodiments of the methods disclosed herein, the compound of Formula I may be administered, for example, from a single dose to multiple doses per week, although in some embodiments the methods of the present invention may be performed by administering the compound of Formula I at a frequency outside this range. In some embodiments, the compound of Formula I may be administered from about once per month to about five times per week. In some embodiments, the compound of Formula I is administered once per week.

Since the compound of Formula I can be formulated to provide reduced systemic levels of the compound while inducing a high levels of cytokines, it is believed to be very useful for providing an enhanced local immune response while minimizing undesirable systemic side effects. This may be advantageous for many uses, such as direct administration to a tumor and/or as a vaccine adjuvant.

Objects and advantages of this invention are illustrated by the above examples, but the particular materials and amounts thereof recited, as well as other conditions and details, should not be construed to unduly limit this invention.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of treating a viral, bacterial, fungal, or parasitic infection in an animal comprising administering an effective amount of a compound having the formula N-(4-{[4-amino-2-butyl-1H-imidazo[4,5-c]quinolin-1-yl]oxy}butyl)octadecanamide, or a pharmaceutically acceptable salt thereof, to the animal.

2. The method of claim 1, which treats a viral infection in an animal.

3. The method of claim 1, which treats a bacterial infection in an animal.

4. The method of claim 1, which treats a fungal infection in an animal.

5. The method of claim 1, which treats a parasitic infection in an animal.

6. The method of claim 1, wherein the compound is co-delivered with a vaccine.

7. The method of claim 1, wherein the treatment is a therapeutic or prophylactic treatment.

8. The method of claim 1, wherein the treatment is a therapeutic treatment.

9. The method of claim 1, wherein the treatment is a prophylactic treatment.

10. The method of claim 1, wherein an antigen is co-delivered with the compound.

11. The method of claim 10, wherein the antigen is a vaccine.

12. The method of claim 10, wherein the antigen is co-delivered with the compound as an admixture in a pharmaceutical composition.

* * * * *

UNITED STATES PATENT AND TRADEMARK OFFICE
CERTIFICATE OF CORRECTION

PATENT NO. : 10,383,938 B2
APPLICATION NO. : 16/043394
DATED : August 20, 2019
INVENTOR(S) : Wightman It is certified that error appears in the above-identified patent and that said Letters Patent is hereby corrected as shown below:

In the Specification

Column 4
Line 33, Delete "N-" and insert -- (N- --, therefor.
Line 34, Delete "octadecanamide" and insert -- octadecanamide) --, therefor.

Column 5
Line 2, Delete "0.198" and insert -- (0.198 g) --, therefor.
Line 60, Delete "(299 g)," and insert -- (2.99 g), --, therefor.

Column 8
Line 47, Delete "Spleenocytes," and insert -- Splenocytes, --, therefor.

Column 10
Line 20, Delete "Spleenocytes," and insert -- Splenocytes, --, therefor.

Column 12
Line 39, Delete "(RNA later" and insert -- (RNAlater --, therefor.

Column 14
Line 57, Delete "cytotoxoid" and insert -- cytotoxic --, therefor.

Column 15
Line 4, Delete "for inflation," and insert -- formulation, --, therefor.
Line 63, Delete "influenzavinis)," and insert -- influenzavirus), --, therefor.

Column 16
Line 16, Delete "carnii," and insert -- carinii --, therefor.
Line 55, Delete "IL-1O" and insert -- IL-10 --, therefor.

Signed and Sealed this
Third Day of March, 2020

Andrei Iancu
*Director of the United States Patent and Trademark Office*

Column 17
Line 61, Delete "close" and insert -- dose --, therefor.